(12) United States Patent
Van Kruchten

(10) Patent No.: US 6,316,571 B1
(45) Date of Patent: Nov. 13, 2001

(54) CARBOXYLATES IN CATALYTIC HYDROLYSIS OF ALKYLENE OXIDES

(75) Inventor: Eugene Marie Godfried Andre Van Kruchten, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/645,724

(22) Filed: Aug. 24, 2000

Related U.S. Application Data

(62) Division of application No. 09/457,533, filed on Dec. 9, 1999, now Pat. No. 6,153,801.

(30) Foreign Application Priority Data

Dec. 14, 1998 (EP) .................................................. 98204234
Apr. 29, 1999 (EP) .................................................. 99201348

(51) Int. Cl.[7] ........................... C07C 29/10; C07C 31/20; C07C 29/32; C07C 29/159
(52) U.S. Cl. ........................................... 526/915; 568/867
(58) Field of Search .............................. 568/867; 526/915

(56) References Cited

U.S. PATENT DOCUMENTS

| 3,933,923 | 1/1976 | Osberghaus et al. ............ 260/615 R |
| 4,160,116 | 7/1979 | Mieno et al. ......................... 568/867 |
| 4,982,021 | 1/1991 | Best et al. ............................. 568/867 |

FOREIGN PATENT DOCUMENTS

| 0156449 A2 | 10/1985 | (EP) | .............. C07C/29/10 |
| 0 226 799 * | 7/1987 | (EP) | .............. C07C/29/10 |
| 0160330 A1 | 11/1985 | (EP) | .............. C07C/31/20 |
| WO 95/20559 | 8/1995 | (WO) | .............. C07C/29/10 |

\* cited by examiner

Primary Examiner—Sreeni Padmanabhan
Assistant Examiner—Brian J. Davis

(57) ABSTRACT

The present invention relates to a process for the preparation of alkylene glycols by reacting an alkylene oxide with water in the presence of a catalytic composition including a polycarboxylic acid derivative, having in its chain molecule one or more carboxyl groups and one or more carboxylate groups, the individual carboxyl and/or carboxylate groups being separated from each other in the chain molecule by a separating group consisting of at least one atom. Preferably the polycarboxylic acid derivative is immobilised on a solid support.

17 Claims, No Drawings

CARBOXYLATES IN CATALYTIC HYDROLYSIS OF ALKYLENE OXIDES

This is a division of application Ser. No. 09/457,533 filed Dec. 9, 1999, now U.S. Pat. No. 6,153,801 disclosed of which is hereby incorporated by reference.

FIELD OF THE INVENTION

The present invention relates to a process for the preparation of alkylene glycols by reacting an alkylene oxide with water in the presence of a catalytic composition.

BACKGROUND OF THE INVENTION

Alkylene glycols, in particular monoalkylene glycols, are of established commercial interest. For example, monoalkylene glycols are being used in anti-freeze compositions, as solvents and as base materials in the production of polyalkyene terephthalates e.g. for fibres or bottles.

The production of alkylene glycols by liquid phase hydrolysis of alkylene oxide is known. The hydrolysis is performed without a catalyst by adding a large excess of water, e.g. 20 to 25 moles of water per mole of alkylene oxide, or it is performed with a smaller excess of water in a catalytic system. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative for increasing the reaction selectivity without having to use a large excess of water. Usually these efforts have focused on the selection of more active hydrolysis catalysts and various catalysts have been disclosed.

Both acid and alkaline hydrolysis catalysts have been investigated, whereby it would appear that the use of acid catalysts enhances the reaction rate without significantly affecting the selectivity, whereas by using alkaline catalysts generally lower selectivities with respect to the monoalkylene glycol are obtained.

Certain anions, e.g. bicarbonate (hydrogen carbonate), bisulphite (hydrogen sulphite), formate and molybdate, are known to exhibit good catalytic activity in terms of alkylene oxide conversion and selectivity towards monoalkylene glycol. However when the salts of these anions are used as the catalyst in a homogeneous system, work-up of the reaction product by distillation will pose a problem because the salts are poorly soluble in the glycol and tend to make it semi-solid. Quaternary ammonium salts remain soluble in the glycol reaction product.

High conversions, good selectivity and a low water/alkylene oxide ratio can be obtained with the process, disclosed in EP-A 0 156 449 and EP-A 0 160 330 (both of Union Carbide). According to these documents the hydrolysis of alkylene oxides is carried out in the presence of a selectivity-enhancing metalate anion-containing material, preferably a solid having electropositive complexing sites having affinity for the metalate anions. The said solid is preferably an anion exchange resin, in particular a styrene-divinyl benzene copolymer. The electropositive complexing sites are in particular quaternary ammonium, protonated tertiary amine or quaternary phosphonium. The metalate anions are specified as molybdate, tungstate, metavanadate, hydrogen pyrovanadate and pyrovanadate anions. A complication of this process is that the alkylene glycol-containing product stream also comprises a substantial amount of metalate anions, displaced from the electropositive complexing sites of the solid metalate anion containing material. In order to reduce the amount of metalate anions in the alkylene glycol product stream, this stream is contacted with a solid having electropositive complexing sites associated with anions which are replaceable by the said metalate anions.

In WO 95/20559, there is disclosed a process for the preparation of alkylene glycols wherein an alkylene oxide is reacted with water in the presence of a catalyst composition comprising a solid material having one or more electropositive sites, which are coordinated with one or more anions other than metalate or halogen anions, e.g. bicarbonate, bisulphite and carboxylate, with the proviso that when the solid material is an anionic exchange resin of the quaternary ammonium type and the anion is bicarbonate the process is performed in the substantial absence of carbon dioxide. According to this document, the presence of carbon dioxide in the feed is detrimental to the catalytic effect of bicarbonate-exchanged resins of the quaternary ammonium type.

A drawback shared by the conventional anionic exchange resins is their limited tolerance to heat. In practising the process of alkylene oxide hydrolysis according to WO 95/20559 with catalyst compositions based on conventional organic quaternary ammonium ion exchangers it has been found, that under severe alkylene oxide hydrolysis reaction conditions (high temperature and/or long service) the catalytic activity (selectivity and/or conversion) of the conventional resin-based catalysts tends to deteriorate. Moreover, under these reaction conditions these catalysts were found to undergo swelling.

In EP-A 226 799 there is disclosed a method for preparing ethylene glycol or propylene glycol by hydration of the respective oxide, in the presence of a dual composition catalyst consisting of a monobasic or polybasic carboxylic acid and a metal or ammonium salt of such a carboxylic acid.

SUMMARY OF THE INVENTION

The present invention relates to a process for the preparation of alkylene glycols by reacting an alkylene oxide with water in the presence of a catalytic composition including a polycarboxylic acid derivative, having in its chain molecule one or more carboxyl groups and one or more carboxylate groups, the individual carboxyl and/or carboxylate groups being separated from each other in the chain molecule by a separating group consisting of at least one atom.

Preferably the number of carboxylic groups in the molecule is at least equal to the number of carboxylate groups.

In a preferred embodiment of the present invention, the polycarboxylic acid derivative as defined above is immobilised on a solid support. Solid catalysts including such immobilised polycarboxylic acid derivatives are novel.

DETAILED DESCRIPTION OF THE INVENTION

The carboxylate groups may be metal salts such as alkali metal and earth alkali metal salts or ammonium salts. Preferably the carboxylates are alkali metal salts, most preferably sodium salts.

The separating group may comprise several atoms, which then may be arranged in a linear or branched chain or in a ring. Preferably the separating group consists of a single carbon atom.

Examples of dicarboxylic acid derivatives according to the invention are the monosodium salts of malonic acid, succinic acid, adipic acid, tartaric acid, maleic acid, terephthalic acid, malic acid, suberic acid, phthalic acid, isophthalic acid, quinolinic acid (2,3 pyridine dicarboxylic acid), isochinchomeronic acid (2,5 pyridine dicarboxylic acid), dipicolinic acid (2,6 pyridine dicarboxylic acid), chinchomeronic acid (3,4 pyridine dicarboxylic acid), dinicotinic acid (3,5 pyridine dicarboxylic acid), cyclohexene-1,2-dicarboxylic acid (3,4,5,6-tetrahydrophtalic acid) and isomers, cyclohexane-1,2-dicarboxylic acid (hexahydrophthalic acid) and isomers, cyclohexane-1,1-dicarboxylic acid, thiophene-2,5-dicarboxylic acid, chelidonic acid (4-oxo-4H-pyran-2,6-dicarboxylic acid), thiophene-3,4-dicarboxylic acid, etc.

Examples of uricarboxylic acid derivatives according to the invention are the monosodium salts of citric acid, trimellitic acid (1,2,4-benzenetricarboxylic acid), and trimesic acid (1,3,5-benzenetricarboxylic acid).

Examples of tetracarboxylic acid derivatives according to the invention are the monosodium and disodium salt of pyromellitic acid (1,2,4,5-benzenetetracarboxylic acid).

As such, the polycarboxylic acid derivative as herein defined are effective as alkylene oxide hydrolysis catalysts in a homogeneous liquid reaction system. However, a particular advantage of these polycarboxylic acid derivatives emerges when they are used in a heterogeneous reaction system, wherein they are immobilised on a solid support, especially but not exclusively a solid material having electropositive sites as defined in WO 95/20559. In particular, when the solid support is a strongly basic anionic exchange resin the anion of which is exchanged with a polycarboxylic acid derivative according to the present invention, a catalytic composition is formed which is stable and which retains its selectivity and stability under severe reaction conditions as well as being more resistant to swelling.

Any of a large number of ion exchange resins (IER's) can be used as the solid support, in particular the strongly basic (anionic) IER's wherein the basic groups are quaternary ammonium or quaternary phosphonium, IER's based on vinylpyridine, polysiloxanes, as well as other solid supports having electropositive complexing sites of inorganic nature, such as carbon, silica, silica-alumina, zeolites, glass and clays such as hydrotalcite. Further, immobilised complexing macrocycles such as crown ethers, etc. can be used as well as solid support.

Anionic exchange resins which are suitable for use in the present process are known per se and many are commercially available, e.g. the ones sold under the trade names AMBERJET 4200, AMBERLITE 400, IRA 404, LEWATIT M 500WS, DOWEX 1×8, DOWEX MSA-1 (all of which are products based on polystyrene, cross-linked with divinylbenzene) and REILLEX HPQ (based on polyvinylpyridine, cross-linked with divinylbenzene).

Custom-made immobilised crown ethers, on and in different solid support materials such as polystyrenes, acrylates and silicas, are presently marketed under the tradename SuperLig by IBC Advanced Technologies Inc., American Fork, Utah, USA.

The catalyst carboxylic acid derivative according to the invention can be immobilised on the solid support by adding it in aqueous solution to a suspension of the solid support, which may or may not be adapted in a foregoing preparatory step. For example, when the solid support is an anionic exchange resin the immobilisation can be performed in a single step by mixing the resin with the catalyst in aqueous medium, followed by washing with water—or alternatively in two steps by first converting the resin to its hydroxyl form with a hydroxide such as aqueous sodium hydroxide, and then adding the catalyst.

The alkylene oxides used as starting material in the process of the invention have their conventional definition, i.e. they are compounds having a vicinal oxide (epoxy) group in their molecules.

Particularly suitable are alkylene oxides of the general formula

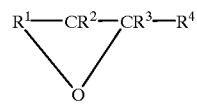

wherein $R^1$ to $R^4$ independently represent a hydrogen atom or an, optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted situted $C_1$–$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane, 2,3-epoxybutane and glycidol. Ethylene oxide and propylene oxide are of particular commercial importance.

As mentioned above, it is advantageous to perform the hydrolysis of the alkylene oxides, without using excessive amounts of water. In the process according to the present invention, amounts of water in the range of 1 to 15 moles per mole of alkylene oxide are quite suitable, amounts in the range of 1 to 6 on the same basis being preferred. In the process of the invention high selectivities with respect to the monoalkylene glycol are often already achieved, when only 4 or 5 moles of water per mole of alkylene oxide are supplied.

The process of the invention may be carried out in batch operation. However, in particular for large scale embodiments it is preferred to operate the process continuously.

Such continuous process can be carried out in a fixed bed reactor, operated in up-flow or down-flow. Down-flow operation is preferred.

The reactor may be maintained under isothermal, adiabatic or hybrid conditions. Isothermal reactors are generally shell- and tube reactors, mostly of the multitubular type, wherein the tubes contain the catalyst and a coolant passes outside the tubes. Adiabatic reactors are not cooled, and the product stream leaving them may be cooled in a separate heat exchanger.

Under certain chosen circumstances the catalytic conversion of EO may be incomplete, in which situation rest EO can be thermally hydrolysed in the dead space of the reactor below the catalyst bed. Since this thermal hydrolysis is less specific towards MEG, it is recommended to minimise the liquid hold-up in the reactor. This can be achieved by filling the reactor outlet part with internals or inert packing material to reduce its volume, and/or by adding an inert gas, such as nitrogen, to the reactor feed mixture and operating the reactor under so-called trickle flow conditions.

In order to obtain adequate time-yield values, it is recommended to perform the process under elevated temperature and pressure conditions.

Suitable reaction temperatures are generally in the range from 80 to 200° C., whereby temperatures in the range from 90 to 150° C. are preferred. The reaction pressure is usually selected in the range of 200 to 3000, preferably 200 to 2000 kPa. For batch operations of the process, the selected reaction pressure is advantageously obtained by pressurising with an inert gas, such as nitrogen. If desired, mixtures of gases may be used, for example a mixture of carbon dioxide and nitrogen is in certain instances advantageous.

In order to accommodate any swelling of the catalyst during operation, the reactor volume can advantageously be greater than the volume occupied by of the catalyst therein, for example 10 to 70 vol % greater.

It will be understood that the process of the present invention is not limited to its operation in the presence of the defined catalyst alone. In certain situations, particularly when operating in continuous-flow manner, it has been found to be advantageous to subject at least part, such as about 30–60 wt %, of the alkylene oxide feed stream to partial thermal hydrolysis in the absence of catalyst, before completing the hydrolysis catalytically. It has been found that partial hydrolysis, even in the absence of a catalyst, is still sufficiently selective towards the monoalkylene glycol while on the other hand this measure is effective in saving the catalyst.

A problem which may occasionally arise in any process wherein ethylene oxide is being hydrolysed is the presence of small amounts of amines and/or phosphines as impurities in the product stream. When a strongly basic anion exchange resin is used as the solid support for the catalytic anion, the basic groups thereof are quaternary ammonium or quaternary phosphonium groups. It has been found that during operation, small amounts of amines or phosphines tend to leach from the resin into the product stream. Besides, amines in the product stream may also originate from corrosion inhibitors which may be added to the water used in the process. Although the amounts of such amine or phosphine contaminants reaching the end-product are generally very small, they may affect the quality of the end-product such that it may be desirable to keep them below the detection level. For example, trimethylamine (TMA) and/or dimethylamine (DMA) may reach the end-product in an amount of up to 10 ppm while the fishy odor of TMA may be detected in an amount as low as 1 ppb.

An effective measure in removing amines and/or phosphines which may be present in the product stream of generally any process wherein ethylene oxide is being hydrolysed, including the process of the present invention, has been found to be the use of a guard-bed, containing a strongly acidic ion exchange resin which effectively captures the amines or phosphines. Strongly acidic ion exchange resins are of the sulphonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB and LEWATIT S 100 G1. These strongly acidic ion exchange resins are available in $H^+$ form and in salt form, such as the $Na^+$ form. When only the $H^+$ form of the strongly acidic resin is used in the guard bed, the product stream after passing it may become acidic. Using a mixture of the strongly acidic ion exchange resin in its $H^+$ form and salt form has the advantage of the pH of the product stream remaining close to neutral.

An added advantage of the strongly acidic guard bed is that any remaining alkylene oxide which may be still present in the product stream is hydrolysed to alkylene glycol, albeit with a lesser selectivity towards the monoalkylene glycol.

In order to accommodate for exhaustion of the strongly acidic ion exchange resin during operation, it is advantageous to operate the guard bed in two or more separate vessels.

Exhausted strongly acidic ion exchange resin can be regenerated by treatment with an acid which is stronger than the sulphonic acid groups in the resin matrix, such as HCl and $H_2SO_4$. Hot sulphuric acid of 0.1–2 normality has been proven to be effective.

The following Examples will illustrate the invention.

EXAMPLES

I. Experiments 1–12, Batch Hydrolysis in Homogeneous Catalytic System

The following carboxylic acid samples and sodium carboxylates were screened for catalytic activity in a batch EO hydrolysis reaction:

Dicarboxylic Acids and Carboxylates

Oxalic acid HOOC—COOH and its mono- and disodium salt

Malonic acid HOOC—$CH_2$—COOH and its monosodium salt

Succinic acid HOOC—$CH_2$—$CH_2$—COOH and its mono- and disodium salt

Tartaric acid HOOC—CH(OH)—CH(OH)—COOH and its mono- and disodium salt

Mono- and disodium salt of maleic acid HOOC—CH=CH—COOH; cis

Adipic acid (HOOC—(CH$_2$)$_4$—COOH) and its monosodium salt

Terephthalic acid p-COOH—C$_6$H$_4$—COOH and its mono- and disodium salt

Tricarboxylic Acids and Carboxylates

Citric acid HOOC—CH$_2$—C(OH)(COOH)—CH$_2$—COOH, its mono-, di- and trisodium salt Trimellitic acid 1,2,4-C$_6$H$_3$(COOH)$_3$ and its mono- and disodium salt Tetracarboxylic Acid and Carboxylates Pyromellitic acid 1,2,4,5-C$_6$H$_2$(COOH)$_4$ and its mono-, di- and trisodium salt A 250 ml autoclave was charged with 30 mmol of polycarboxylic acid derivative or the comparative sodium bicarbonate and 5.55 mol (100 g) of water. Some of the carboxylic acid derivatives were purchased as the hydrates and used as such. The amount of water introduced to the reaction system by these hydrates (max. 210 mmol), however, was considered to be insignificant and no adjustment of water intake was made.

The gascap was purged 3 times with nitrogen and an initial pressure of 1000 kPa was employed. The mixture was heated to 100° C. Ethylene oxide (44 g; 1 mol) was slowly added under stirring at 500 rpm. The reaction mixture was maintained under continuous stirring for 6 hours at 100° C. An end of run sample was taken for GLC analysis.

The results of the catalytic EO batch hydrolysis experiments in terms of selectivity to MEG, using the homogeneous catalysts (carboxylic acids and sodium carboxylates) and the results of reference experiments (no catalyst and NaHCO$_3$) are summarised in Table 1.

TABLE 1

| Exp. No. | Catalyst | Selectivity towards MEG (mol %)* | | | |
|---|---|---|---|---|---|
| | | acid | mono-Na | di-Na | tri-Na |
| | References | | | | |
| 1 | — | 67.8 | | | |
| 2 | NaHCO$_3$ | 85.0 | | | |
| | Dicarboxylic derivatives | | | | |
| 3 | oxalic acid | 77.0 | 78.2 | 78.7 | |
| 4 | malonic acid | 73.7 | 83.1 | | |
| 5 | succinic acid | 72.2 | 82.7 | 53.1 | |
| 6 | maleic acid | | 83.2 | 48.9 | |
| 7 | tartaric acid | 72.5 | 82.4 | 66.0 | |
| 8 | adipic acid | 72.3 | 80.3 | | |
| 9 | terephthalic acid | 70.8 | 82.6 | 51.0 | |
| | Tricarboxylic derivatives | | | | |
| 10 | citric acid | 70.9 | 85.4 | 76.7 | 43.3 |
| 11 | trimellitic acid | 74.5 | 84.3 | 64.8 | |
| | Tetracarboxylic derivatives | | | | |
| 12 | pyromellitic acid | 74.7 | 83.9 | 84.6 | 72.7 |

*Selectivity towards MEG (mol %) = 100 × MEG/(MEG + 2DEG + 3TEG), measured at >99.5% EO conversion The results indicate that in all cases the polycarboxylic acids perform only slightly better than the thermal non-catalysed reaction (70.8–77.0 vs. 67.8% selectivity to MEG).

Except for oxalic acid, a significant improvement in MEG selectivity (to 80.3–85.4%) is obtained when the mono sodium salts of a dicarboxylic acid are used as a catalyst. However, when both carboxylic acid groups of a dicarboxylic acid are converted into carboxylate groups the selectivity becomes inferior (48.9–66.0%).

A similar behaviour is observed for the tricarboxylic acids: an optimum selectivity for the mono sodium salts (84–85%) and an inferior selectivity for the trisodium analogues. Also the disodium carboxylates of tricarboxylic acids show a decrease in selectivity (although less pronounced) when compared with the corresponding mono sodium salts (64.8/76.7 vs 85%).

The tetracarboxylic acid (pyromellitic acid) behaves similarly, both the mono- and disodium carboxylates in this case exhibiting the optimal selectivity performance (83.9/84.6%).

II. Experiments 13–17, Batch Hydrolysis in Heterogeneous Catalytic System

Two strongly basic ion exchange resins of the quaternary ammonium type were used:

AMBERJET 4200, a mono-disperse cross-linked polystyrene/divinylbenzene based resin ex Rohm and Haas, chloride form, exchange capacity 1.4 meq/ml, and IRA 404, a poly-disperse cross-linked polystyrene/divinylbenzene based resin ex Rohm and Haas, chloride form, exchange capacity 1.3 meq/ml.

The resin was treated as follows to immobilise the carboxylic acid derivative:

150 ml of wet resin was slurried in a water filled glass tube (60×2.5 cm);

chloride was exchanged by treatment with sodium bicarbonate (reference), monosodium citrate (according to the invention)or trisodium citrate (reference), in each case in aqueous solution (10 molar excess, in 2500 g of water) for approximately 5 hours (LHSV: 4 l/h);

the exchanged resin was washed with 1200 ml of water for 2 hours (LHSV: 4 l/h);

by this procedure most (>98%) of the chlorine anions in the resin were exchanged by the desired anion.

A 250 ml autoclave was filled with the catalyst (30 mmol) and water (100 g; 5.55 mol). The gascap was purged 3 times with nitrogen and an initial pressure of 1000 kPa was employed. The mixture was heated to 100° C. Ethylene oxide (44 g; 1 mol) was slowly added under stirring (500 rpm). The reaction mixture was maintained under continuous stirring for 6 hours at 100° C. An end of run sample was taken for GLC analysis.

The results (EO conversion and MEG selectivity data) are summarised in Table 2.

TABLE 2

| Exp. No. | Catalyst | Amount of catalyst (mmol) | EO conversion* (%) | selectivity towards MEG (%)** |
|---|---|---|---|---|
| 13 (ref.) | — | — | 99.2 | 67.8 |
| 15 (ref.) | AMBERJET 4200/ HCO$_3^-$ | 30 | 99.0 | 88.3 |

TABLE 2-continued

| Exp. No. | Catalyst | Amount of catalyst (mmol) | EO conversion* (%) | selectivity towards MEG (%)** |
|---|---|---|---|---|
| 16 | AMBERJET 4200/ citrate mono-anion | 30 | 99.5 | 79.3 |
| 17 | IRA 404/ citrate mono-anion | 30 | 99.6 | 79.8 |
| 18 (ref) | AMBERJET 4200/ citrate tri-anion | 30 | 99.7 | 58.3 |

*: EO conversion (%) = 100% * (MEG + 2DEG + 3TEG)/(EO + MEG + 2DEG + 3TEG)
**: Selectivity towards MEG (%) = 100 × MEG/(MEG + 2DEG + 3TEG)

The results in Table 2 indicate that, similarly to the findings in a homogeneous catalytic system, also in a heterogeneous system the partial salt of the polycarboxylic acid is a satisfactorily selective catalyst while the complete salt is not.

III. Experiments 19–20, Catalyst Stability Test

The thermal stability of an AMBERJET 4200/carboxylate catalysts was evaluated and compared with the thermal stability of AMBERJET 4200/bicarbonate. The thermal stability was tested by placing 20 ml of the catalyst in a 65 cm long, 0.5 inch wide Hoke tube, provided with a heating jacket using a hot oil system. Water was pumped with an HPLC pump with an LHSV of 1 l/l.h over the catalyst bed at 150° C. and a pressure of 1000 kPa during 48 hours. Then the catalyst sample was removed from the reactor. The strongly basic capacity (quaternary ammonium groups), the weakly basic capacity (tertiary amine groups) and the total anion capacity (the sum of the two previous capacities) in the fresh and used catalyst were determined by titration and the % difference (change during use) noted.

The results are summarised in Table 3.

(water:EO molar ratio between 5.0 and 18.9; LHSV between 0.81–0.95 and maximum bed temperature between 95–112° C.). Samples were taken periodically.

The results are summarised in Table 4.

TABLE 4

| Run hour (h) | H₂O/EO mol ratio | LHSV (l/l · h) | Max. bed Temperature (° C.) | EO conversion (mol %)* | selectivity towards MEG (mol %)** |
|---|---|---|---|---|---|
| 75 | 8.1 | 0.91 | 112 | 98.8 | 97.7 |
| 107 | 8.1 | 0.88 | | 99.3 | 96.7 |
| 153 | 8.0 | 0.89 | | 99.3 | 96.8 |
| 223 | 11.9 | 0.90 | | 100.0 | 97.4 |
| 270 | 12.1 | 0.94 | 103 | 99.7 | 97.8 |
| 317 | 18.9 | 0.95 | 105 | 100.0 | 98.4 |
| 392 | 18.8 | 0.95 | 107 | 100.0 | 98.3 |
| 417 | 5.0 | 0.85 | 103 | 97.2 | 93.8 |
| 465 | 13.5 | 0.90 | | 100.0 | 97.0 |
| 486 | 12.1 | 0.91 | 102 | 99.8 | 97.7 |
| 528 | 5.1 | 0.87 | | 97.7 | 94.5 |
| 704 | 5.0 | 0.82 | 102 | 98.3 | 95.3 |
| 772 | 5.0 | 0.87 | | 97.5 | 96.0 |
| 847 | 5.0 | 0.81 | 95 | 96.9 | 96.3 |

*EO conversion (mol %) = 100 × (MEG + 2DEG + 3TEG)/(EO + MEG + 2DEG + 3TEG)
**Selectivity towards MEG (mol %) = 100 × MEG/(MEG + 2DEG + 3TEG)

V. Experiments 22 and 23, Continuous EO Hydrolysis

AMBERJET 4200/citrate mono-anion catalyst was used in continuous fixed-bed experiment. The long-time performance was compared with that of AMBERJET 4200/bicarbonate under exactly identical process conditions.

The experiments were carried out in a once-through mode. The 24 cm long reactor consisted of a 20 mm (inner diameter) wide glass tube in a 34 mm wide stainless steel metal pipe. Between the glass reactor tube and the SS outer-tube a Teflon (PTFE) layer was used as an insulator. An electrical heating system was used at the outer SS tube to compensate for heat losses; the temperature set point for

TABLE 3

| | Strongly basic capacity (mmol/g) | | | Weakly basic capacity (mmol/g) | | | Total anion capacity (mmol/g) | | |
|---|---|---|---|---|---|---|---|---|---|
| Exp. No. Catalyst | 150° C. t = 0 h | 150° C. t = 48 h | % change | 150° C. t = 0 h | 150° C. t = 48 h | % change | 150° C. t = 0 h | 150° C. t = 48 h | % change |
| 19 AMBERJET 4200/Bicarbonate | 3.19 | 1.15 | −64 | 0.27 | 0.68 | +152 | 3.46 | 1.83 | −47 |
| 20 AMBERJET 4200/citrate mono-anion | 3.19 | 2.23 | −30 | 0.27 | 0.46 | +70 | 3.46 | 2.69 | −22 |

These results indicate that in this severe accelerated stability test the IER/citrate mono-anion catalyst is more than 2 times more stable than the corresponding bicarbonate catalyst.

IV. Experiment 21, Continuous Hydrolysis in a Heterogeneous Catalytic System AMBERJET 4200/citrate mono-anion catalyst was used in this test, wherein process parameters were varied this heating device was set at the temperature of the water/EO reactor feed. The reactor was charged with 60 ml of catalyst. The water feed was preheated to achieve the desired reactor inlet temperature prior to mixing with EO. The temperature of the feed was measured using a thermocouple placed on top of the reactor and the outlet temperature was measured using a thermocouple just below the catalyst bed in the reactor outlet.

The process conditions during these experiments are compiled in Table 5.1.

TABLE 5.1

| | |
|---|---|
| Pressure (kpa) | 1000 |
| Reactor inlet temperature (° C.) | 65–90 |
| Reactor outlet temperature (° C.) | 85–110 |
| H2O/EO flow (ml/h) | 130–150 |
| Mol ratio H$_2$O/EO (mol/mol) | 10–25 |
| LHSV (l/l.h) | 2.3–2.5 |

The results of this comparative experiment are compiled in Table 5.2 and 5.3, showing that the AMBERJET 4200/citrate catalyst has a significantly increased lifetime under the process conditions applied when compared with the corresponding bicarbonate catalyst.

TABLE 5.2

AMBERJET 4200/bicarbonate catalyst

| Run hour (h) | EO conversion (%) |
|---|---|
| 90 | 99.8 |
| 425 | 99.7 |
| 670 | 99.9 |
| 750 | 98.3 |
| 1000 | 99.1 |
| 1200 | 99.2 |
| 1365 | 99.5 |
| 1400 | 96.2 |
| 1600 | 94.7 |
| 1675 | 76.3 |

TABLE 5.3

AMBERJET 4200/citrate catalyst

| Run hour (h) | EO conversion (%) |
|---|---|
| 90 | 99.9 |
| 425 | 99.9 |
| 670 | 99.8 |
| 750 | 99.9 |
| 1000 | 99.7 |
| 1200 | 99.9 |
| 1365 | 99.7 |
| 1400 | 99.7 |
| 1600 | 99.7 |
| 1745 | 99.6 |
| 1895 | 99.6 |
| 1944 | 99.6 |
| 2060 | 99.4 |
| 2350 | 99.3 |
| 2500 | 98.9 |

What is claimed is:

1. A catalyst composition immobilised on a solid support, said catalyst composition comprising a polycarboxylic acid derivative having in its chain molecule one or more carboxyl groups and one or more carboxylate groups, the individual carboxyl and/or carboxylate groups being separated from each other in the chain molecule by at least one atom.

2. The catalyst composition according to claim 1, wherein the atom is a single carbon atom.

3. The catalyst composition according to claim 1, wherein the polycarboxylic acid derivative is a citric acid derivative.

4. The catalyst composition according to claim 1, wherein the citric acid derivative is the mono-anion of citric acid.

5. The catalyst composition according to claim 1, wherein the polycarboxylic acid derivative comprise a dicarboxylic acid derivative.

6. The catalyst composition according to claim 1, wherein the solid support is one having electropositive sites.

7. The catalyst composition according to claim 1, wherein the solid support is an anionic exchange resin of the quaternary ammonium or quaternary phosphonium type.

8. The catalyst composition according to claim 1, wherein the solid support is a clay.

9. The catalyst composition according to claim 1, wherein the solid support comprises an immobilised macrocycle.

10. The catalyst composition according to claim 1, wherein the number of carboxylic groups in the molecule is at least equal to the number of carboxylate groups.

11. The catalyst composition according to claim 1, wherein the carboxylates are alkali metal salts.

12. The catalyst composition according to claim 11, wherein the carboxylates are sodium salts.

13. The catalyst composition according to claim 1, wherein said at least one atom comprises more than one atom arranged in a linear or branched chain or in a ring.

14. The catalyst composition according to claim 5, wherein the dicarboxylic acid derivative comprises monosodium salt selected from the group consisting of monosodium salts of malonic acid, succinic acid, adipic acid, tartaric acid, maleic acid, terephthalic acid, malic acid, suberic acid, phthalic acid, isophthalic acid, quinolinic acid (2,3 pyridine dicarboxylic acid), isochinchomeronic acid (2,5 pyridine dicarboxylic acid), dipicolinic acid (2,6 pyridine dicarboxylic acid), chinchomeronic acid (3,4 pyridine dicarboxylic acid), dinicotinic acid (3,5 pyridine dicarboxylic acid), cyclohexene-1,2-dicarboxylic acid (3,4,5,6-tetrahydrophtalic acid) and isomers, cyclohexane-1,2-dicarboxylic acid (hexahydrophthalic acid) and isomers, cyclohexane-1,1-dicarboxylic acid, thiophene-2,5-dicarboxylic acid, chelidonic acid (4-oxo-4H-pyran-2,6-dicarboxylic acid), and thiophene-3,4-dicarboxylic acid.

15. The catalyst composition according to claim 11, wherein the polycarboxylic acid derivative comprises monosodium salt selected from the group consisting of monosodium salts of citric acid, trimellitic acid (1,2,4-benzenetricarboxylic acid), and trimesic acid (1,3,5-benzenetricarboxylic acid).

16. The catalyst composition according to claim 1, wherein the polycarboxylic acid derivative comprises salt selected from the group consisting of monosodium salts of pyromellitic acid and disodium salts of pyromellitic acid.

17. The catalyst composition according to claim 5, wherein the dicarboxylic acid derivative comprises a salt selected from the group consisting of monosodium salts of oxalic acid, malonic acid, succinic acid, tartaric acid, maleic acid, adipic acid, and terephthalic acid.

* * * * *